(12) United States Patent
Ferry (10) Patent No.: US 9,410,920 B2
(45) Date of Patent: Aug. 9, 2016

(54) APPARATUS AND ITS ARRANGEMENT WITH DUCT TO DETERMINE FLOWABLE MEDIUM PARAMETERS

(71) Applicant: ALSTOM Technology Ltd, Baden (CH)

(72) Inventor: Allan Gunn Ferry, Windsor, CT (US)

(73) Assignee: ALSTOM TECHNOLOGY LTD, Baden (CH)

( * ) Notice: Subject to any disclaimer, the term of this patent is extended or adjusted under 35 U.S.C. 154(b) by 377 days.

(21) Appl. No.: 13/914,791

(22) Filed: Jun. 11, 2013

(65) Prior Publication Data

US 2014/0360249 A1    Dec. 11, 2014

(51) Int. Cl.
　　*G01N 33/00* (2006.01)
　　*G01N 27/407* (2006.01)
　　*G01K 13/02* (2006.01)

(52) U.S. Cl.
　　CPC ............ *G01N 27/4073* (2013.01); *G01K 13/02* (2013.01); *G01N 33/0004* (2013.01)

(58) Field of Classification Search
　　CPC ................... G01N 22/0004; G01N 22/0009
　　See application file for complete search history.

(56) References Cited

U.S. PATENT DOCUMENTS

| | | | |
|---|---|---|---|
| 1,246,799 A | 11/1917 | Wilson | |
| 2,140,562 A * | 12/1938 | Snow | G01F 25/0053 73/1.16 |
| 3,600,933 A * | 8/1971 | Johnston | G01N 25/04 374/23 |
| 4,155,245 A * | 5/1979 | Coe | G01N 25/68 374/21 |
| 5,106,203 A | 4/1992 | Napoli et al. | |
| 5,217,692 A * | 6/1993 | Rump | G01N 33/0031 73/31.05 |
| 2004/0042527 A1 | 3/2004 | Block et al. | |
| 2006/0289308 A1* | 12/2006 | Shaddock | F01N 13/08 204/424 |
| 2007/0137318 A1 | 6/2007 | Desrochers et al. | |

FOREIGN PATENT DOCUMENTS

| | | |
|---|---|---|
| DE | 38 43 233 A1 | 6/1990 |
| DE | 44 38 523 C1 | 12/1995 |

* cited by examiner

*Primary Examiner* — Michael A Lyons
*Assistant Examiner* — Alex Devito
(74) *Attorney, Agent, or Firm* — GE Global Patent Operation; Stephen G. Midgley (57) ABSTRACT

An apparatus is mountable to a duct having a cross-section, for determining parameters of a flowable medium flowing through the duct. The apparatus includes a mounting attachment having a conduit member, and at least one combination of multiple sensing members configured to the conduit member. The conduit member may be disposed entirely within the duct such that the multiple sensing members are located within the duct establishing direct contact with the flowable medium. The multiple sensing members include oxygen and temperature sensing elements respectively, to determine parameter such as oxygen level in the flowable medium, and temperature of the flowable medium. Several such apparatus may be mounted in the duct across the cross-section to define a grid to determine said parameter at various locations across the cross-section.

20 Claims, 6 Drawing Sheets

APPARATUS AND ITS ARRANGEMENT WITH DUCT TO DETERMINE FLOWABLE MEDIUM PARAMETERS

TECHNICAL FIELD

The present disclosure relates to sensing devices and attachments, and, more particularly, to an apparatus and a method to determine various parameters of a flowable medium flowing through a duct.

BACKGROUND

More often than not, it has been in practice to measure a temperature of a flowable medium flowing through duct to have constant check over the flowable medium. Sensing devices, generally attached through suitable fittings or attachments to the ducts, are adapted to determine temperature of the flowable medium flowing through the ducts in order to have constant check of the flowable medium. The sensing devices may generally be placed inside or outside of the duct to determine temperature of the flowable medium. Irrespective of the placement of the sensing devices, challenges have always been in term of accuracy in determining the temperature of the flowable medium, which may arise due to, including but not limited to, improper placement of the sensing devices along or across the duct, improper selection of the sensing devices and appropriate number and positioning of the sensing devises either within or outside of the duct. Further, such conventional sensing devices have also been generally limited for determining a single parameter, such as temperature, oxygen, pressure, etc. of the flowable medium, ignoring the fact that various other parameter may also at the same time would be required to determine the condition of the flowable medium. Furthermore, the fittings or attachments utilized for attaching the sensing devices may also have been quite complicated or uneconomical.

Such conventional sensing devices with fittings may have generally been considered satisfactory for their intended purposes, but may be unsatisfactory in terms of accuracy of temperature of flowable medium and freedom of choice of selection to determine variable parameters of the flowable medium, and placement of the sensing devices over the duct in uneconomical and complicated manner. Accordingly, there exists a need to determine variable parameters of the flowable medium and placement of the sensing devices over the duct in an economical and effective manner.

SUMMARY

The present disclosure describes an apparatus and its arrangement within a duct or a pipe to determine flowable medium parameters, that will be presented in the following simplified summary to provide a basic understanding of one or more aspects of the disclosure that are intended to overcome the discussed drawbacks, but to include all advantages thereof, along with providing some additional advantages. This summary is not an extensive overview of the disclosure. It is intended to neither identify key or critical elements of the disclosure, nor to delineate the scope of the present disclosure. Rather, the sole purpose of this summary is to present some concepts of the disclosure, its aspects and advantages in a simplified form as a prelude to the more detailed description that is presented hereinafter.

An object of the present disclosure is to describe an apparatus, which may be capable in accuracy of temperature and oxygen determination of flowable medium and capable of having freedom of choice of selection to determine variable parameters of the flowable medium. Further object of the present disclosure is to describe an apparatus that is capable of being placed or arranged with a duct in economical and convenient to use. Various other objects and features of the present disclosure will be apparent from the following detailed description and claims.

The above noted and other objects, in one aspect, may be achieved by an apparatus for determining at least one parameter of a flowable medium flowing through a duct. In other aspects, above noted and other objects, may be achieved by an arrangement between the apparatus and the duct, and a system for determining at least one parameter of a flowable medium flowing through a duct.

According to the above aspects of the present disclosure, an apparatus mountable to a duct having a cross-section, for determining at least one parameter of a flowable medium flowing through the duct is disclosed. The apparatus includes a mounting attachment and at least one combination of multiple sensing members configured thereto. Specifically, the mounting attachment includes a conduit member, which has first and second end portions, opposite to each other. Each of the first and second end portions has an opening. The conduit member comprises through hollow and elongated configuration configured to transversely extend entirely into the duct via aligned opposite holes, such that each of the holes matches the respective openings to define a passageway to enable a fluid flow therethrough to provide a reference fluid adapted to determine the at least one parameter; and to cool the apparatus heated by the heated flowable medium flowing through the duct. Further, the at least one combination of multiple sensing members adapted to be disposed specifically on the conduit member such that upon configuring the mounting attachment with the duct, the at least one combination of multiple sensing members is located within the duct to directly being in contact with the flowable medium flowing though the duct to determine the respective parameters of the flowable medium. The at least one combination of multiple sensing members includes at least one oxygen sensing element and at least one temperature sensing element. The at least one oxygen sensing element is capable of determining a level of oxygen in the flowable medium flowing through the duct, and the at least one temperature sensing element is capable of determining the temperature of the flowable medium flowing through the duct.

In one embodiment, a plurality of combination of multiple sensing members may be disposed on the conduit members. Specifically, the plurality of combination of multiple sensing members may spaced apartly be disposed across the conduit members such that upon configuring the mounting attachment with the duct, each of the plurality of combination of multiple sensing members disposed on the conduit member is located within the duct to determine respective parameters across the entire diameter of the duct.

In an embodiment, the one or various combination of multiple sensing member(s) is coupled to the conduit member through a connector such that through hollow configuration of the conduit member remains. The connector may be a T-shaped hollow threaded connector that may include two opposite lateral openings and a transversal opening. The lateral openings are couple to the conduit member and the transversal opening incorporates the least one combination of multiple sensing members. The T-shaped hollow threaded connector is connected to the bifurcated conduit member.

In one embodiment, the combination of multiple sensing members may include two oxygen sensing element and one temperature sensing element disposed therebetween. The oxygen sensing element may, without limiting, be an automotive heated Zirconium oxide sensor. Further, temperature sensing element may, without limiting, be a thermocouple. The parameter of a flowable medium that may be determined, including but not limited to, oxygen level and temperature of the flowable medium using said suitable sensing members. The additional parameters, such as level of carbon monoxide in the flowable medium or flow velocity of the flowable medium or other related parameter may also be determined by the system upon arrangement of suitable sensing member, without departing from the scope of the present disclosure. In such embodiment, the at least one combination of multiple sensing members includes at least one auxiliary sensing element to determine additional parameters, such as level of carbon monoxide in the flowable medium or flow velocity of the flowable medium or other related parameter.

In one embodiment of the present disclosure, the mounting attachment includes a fixture arrangement to releasably and movably mount the mounting attachment to the duct across each of the holes. The fixture arrangement includes a bolt-flange assembly adapted to releasably attach the first end portion of the conduit member to the duct across one of the hole. The fixture arrangement also includes a slip-fit assembly adapted to releasably and movably attach the second end portion of the conduit member to the duct across the other hole. The slip-fit assembly is adapted to enable movement of the second end portion to adjust differential length of the conduit member versus the duct 200 which arises due to heating effect of the flowable medium flowing across the duct.

In one embodiment of the present disclosure, the bolt-flange assembly may include a fan configured at the first end portion along the opening for regulating a desired fluid flow through the passageway.

The passageway on one hand is capable of enabling the fluid from the fan to flow therethrough to serve as a reference for a parameter determined by the sensing members. Based on the fluid flow from the fan flowing through the passageway, the sensing member is configured and adapted to compare a percentage of parameter determined by the sensing member, in the flowable medium flowing through the duct verses a percentage of parameter of the fluid flowing through the passageway. This comparison may also be used to verify whether or not the sensing members are working, and to periodically calibrate thereto online.

On the other hand, the passageway may be capable of enabling the fluid from the fan to flow therethrough to cool the apparatus, which may be heated due to heating effect of the flowable medium flowing through the duct.

In one embodiment of the present disclosure, the apparatus may also include an air nozzle member. The air nozzle member is configured to the mounting attachment to periodically clean the at least one combination of multiple sensing members. The air nozzle member may also be utilized for injecting reference fluid for calibration and verifying sensor working condition. In further embodiment, the apparatus may further includes a protective filter member, which may be configured to be installed over the at least one combination of multiple sensing members. The air nozzle member and the protective filter member both are capable of controlling dust deposition to minimize fouling and plugging of the combination of multiple sensing members.

In another aspect of the present disclosure, an arrangement between the apparatus as disclosed above and duct, is disclosed. In further aspect of the present disclosure, a system incorporating the arrangement between the apparatus and duct, and an electronic module for determining at least one parameter of a flowable medium flowing through the duct, is disclosed.

These together with the other aspects of the present disclosure, along with the various features of novelty that characterize the present disclosure, are pointed out with particularity in the present disclosure. For a better understanding of the present disclosure, its operating advantages, and its uses, reference should be made to the accompanying drawings and descriptive matter in which there are illustrated exemplary embodiments of the present disclosure.

BRIEF DESCRIPTION OF THE DRAWINGS

The advantages and features of the present disclosure will be better understood with reference to the following detailed description and claims taken in conjunction with the accompanying drawing, wherein like elements are identified with like symbols, and in which:

Like reference numerals refer to like parts throughout the description of several views of the drawings.

DETAILED DESCRIPTION

For a thorough understanding of the present disclosure, reference is to be made to the following detailed description, including the appended claims, in connection with the above described drawings. In the following description, for purposes of explanation, numerous specific details are set forth in order to provide a thorough understanding of the present disclosure. It will be apparent, however, to one skilled in the art that the present disclosure can be practiced without these specific details. In other instances, structures and apparatuses are shown in block diagrams form only, in order to avoid obscuring the disclosure. Reference in this specification to "one embodiment," "an embodiment," "another embodiment," "various embodiments," means that a particular feature, structure, or characteristic described in connection with the embodiment is included in at least one embodiment of the present disclosure. The appearance of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but may not be of other embodiment's requirement.

Although the following description contains many specifics for the purposes of illustration, anyone skilled in the art will appreciate that many variations and/or alterations to these details are within the scope of the present disclosure. Similarly, although many of the features of the present disclosure are described in terms of each other, or in conjunction with each other, one skilled in the art will appreciate that many of these features can be provided independently of other features. Accordingly, this description of the present disclosure is set forth without any loss of generality to, and without imposing limitations upon, the present disclosure. Further, the relative terms, such as "first," "second," and the like, herein do not denote any order, elevation or importance, but rather are used to distinguish one element from another. Further, the terms "a" and "an" herein do not denote a limitation of quantity, but rather denote the presence of at least one of the referenced item.

Figure 1:
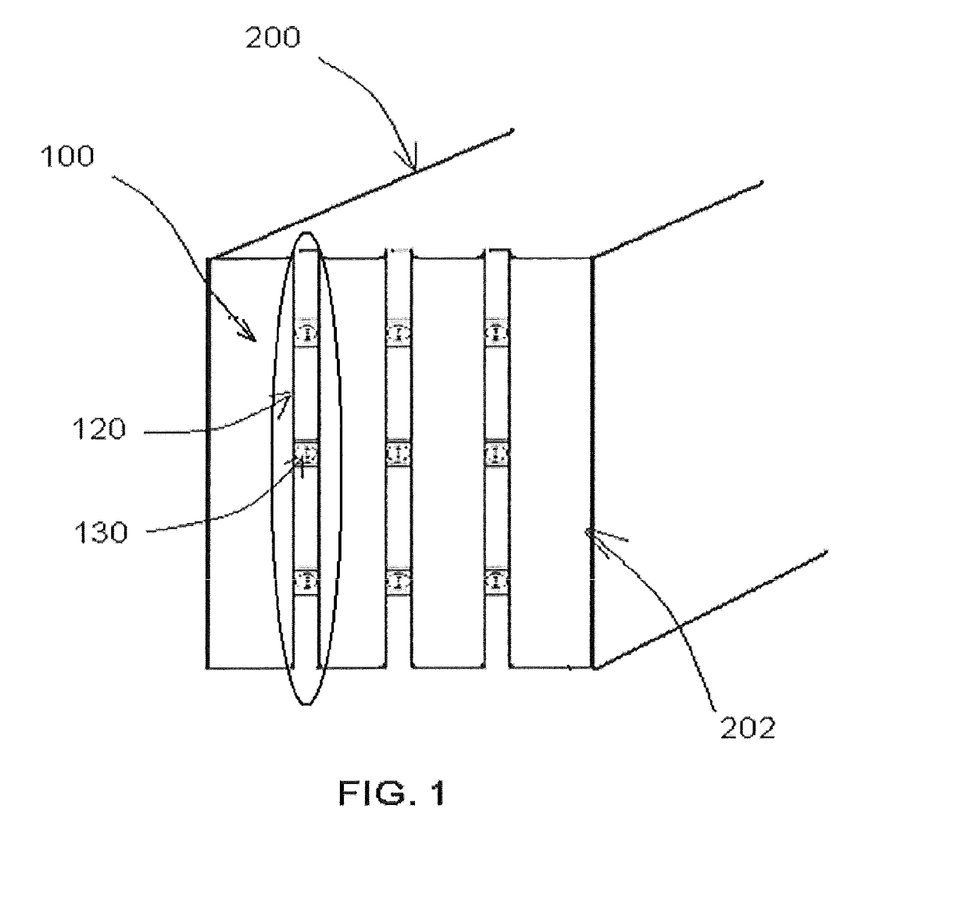
FIG. 1 illustrates an example of an apparatus (encircled) for determining at least one parameter of a flowable medium flowing through a duct, in accordance with an exemplary embodiment of the present disclosure.
Figure 2:
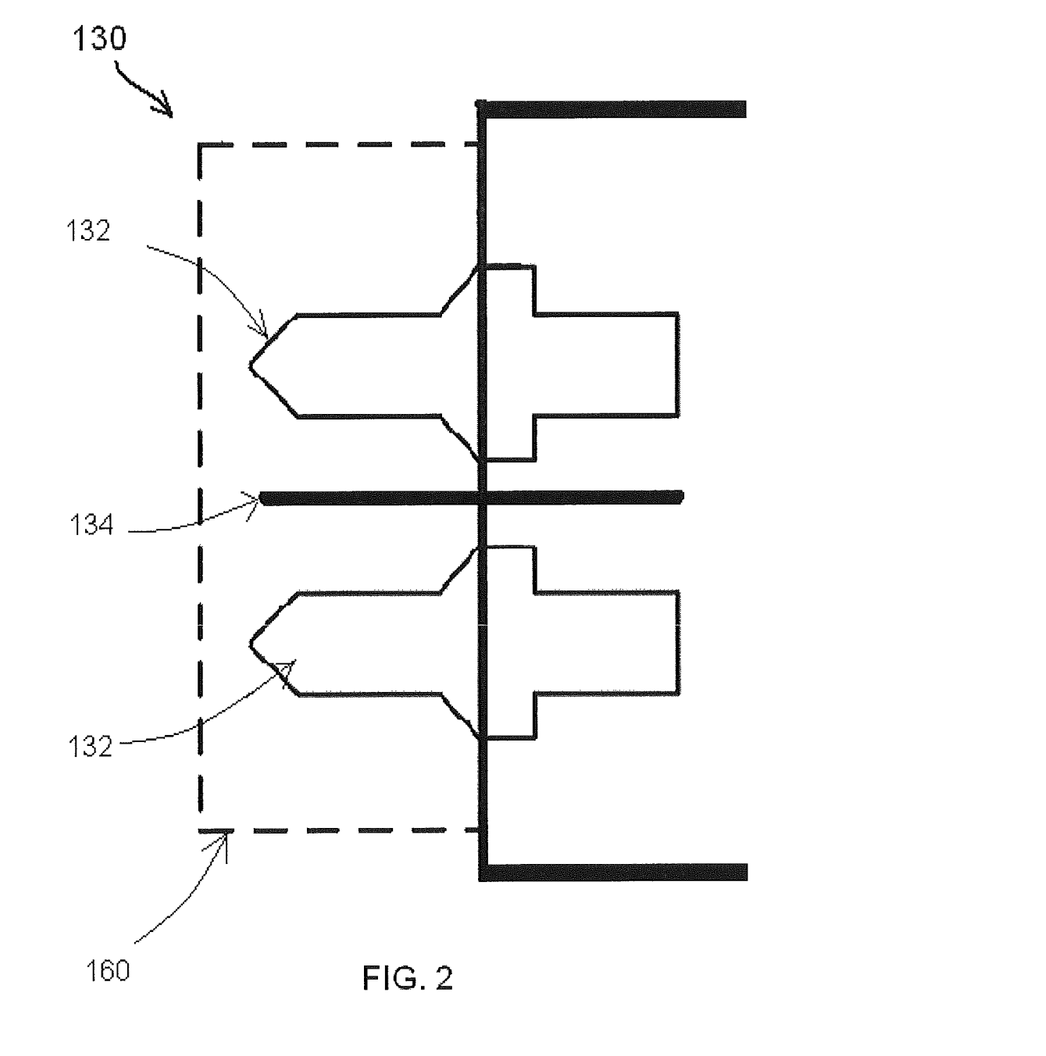
FIG. 2 illustrates a top view of an example of a combination of multiple sensing members of the apparatus of FIG. 1, in accordance with another exemplary embodiment of the present disclosure.
Figure 3A:
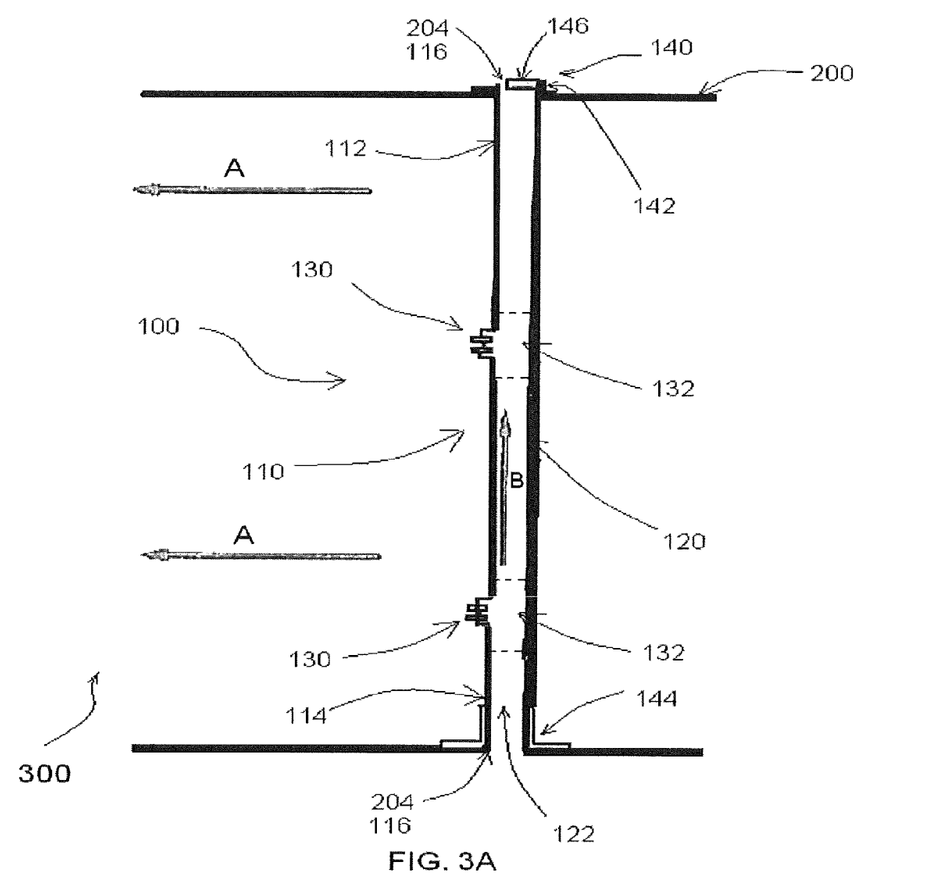
FIGS. 3A and 3B, respectively, illustrate side and rear views of an arrangement between the apparatus of FIG. 1 and a duct, in accordance with an exemplary embodiment of the present disclosure.
Figure 3B:
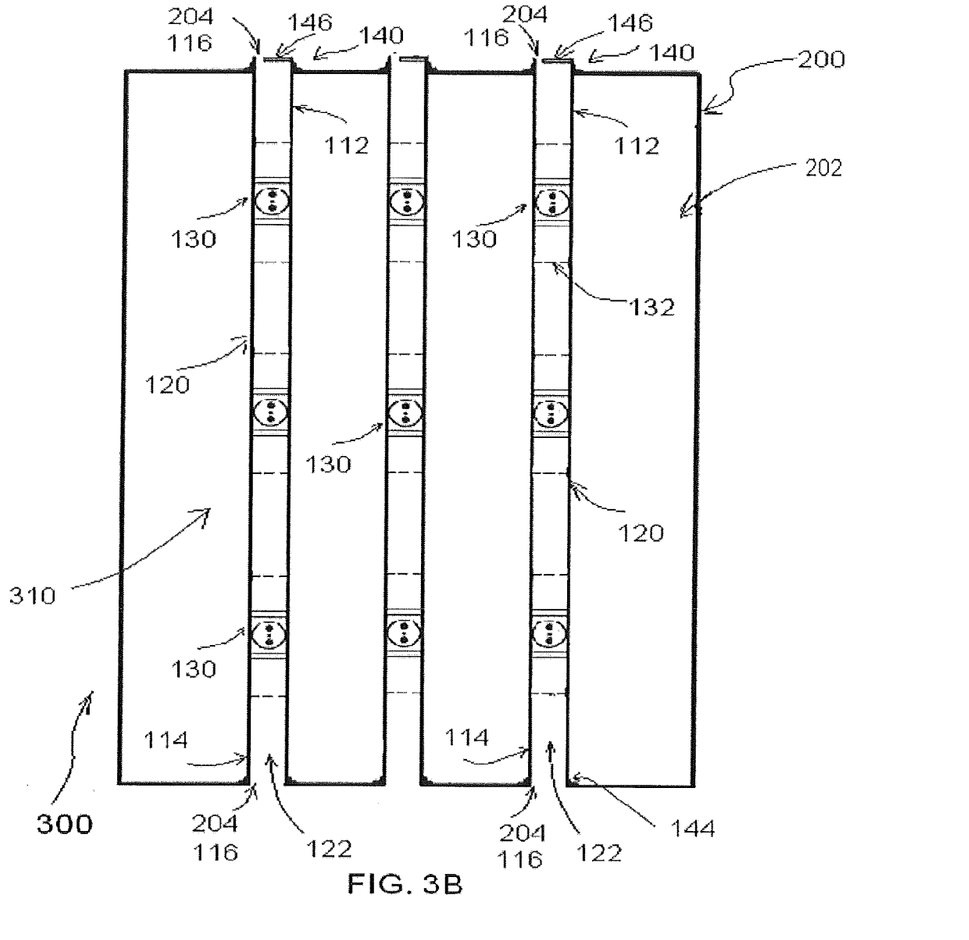
Figure 4:
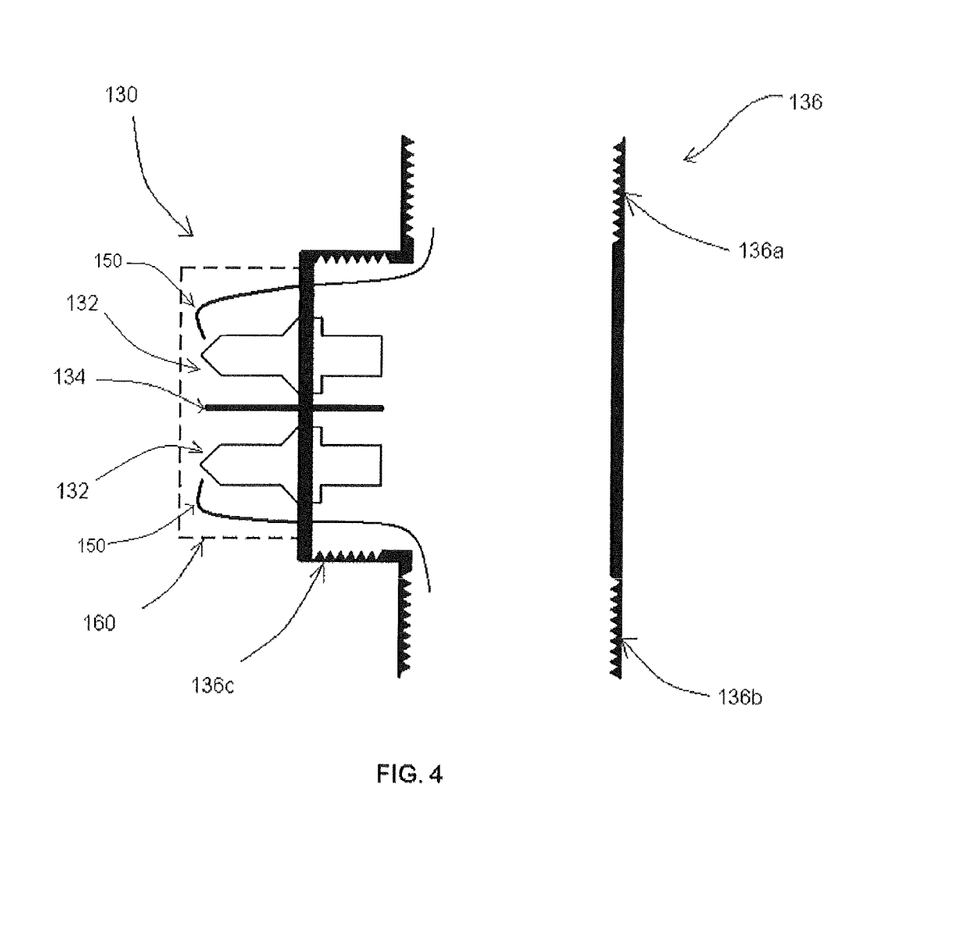
FIG. 4 illustrates a combination of multiple sensing members and its example connecting feature, in accordance with an exemplary embodiment of the present disclosure.
Figure 5:
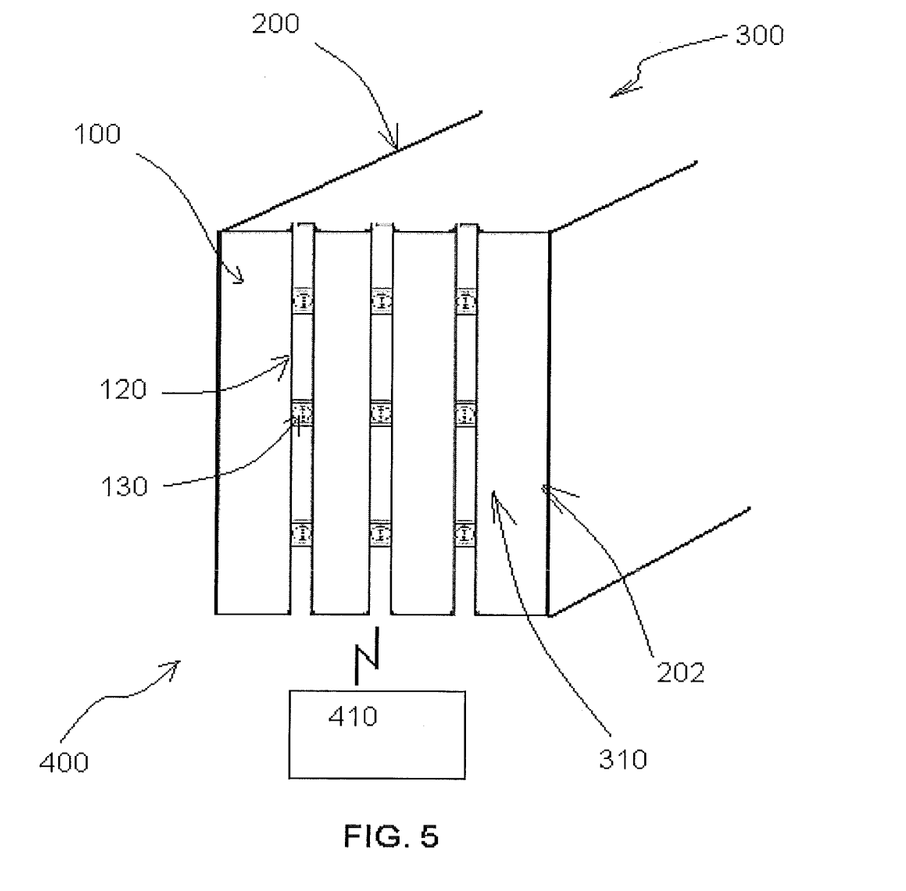
FIG. 5 illustrates a block diagram depicting a system for determining at least one parameter of a flowable medium flowing through a duct, in accordance with an exemplary embodiment of the present disclosure.

Referring now to FIGS. 1 to 5, examples of an apparatus 100 for or determining parameters of a flowable medium flowing through the duct 200, are illustrated in accordance with an exemplary embodiment of the present disclosure. FIG. 1 illustrates a perspective of the apparatus 100 in coordination with the duct 200, whereas FIG. 2 illustrates a combination of multiple sensing members of the apparatus 100 of FIG. 1. Further, FIGS. 3A and 3B illustrate specifically the apparatus 100 assembled to the duct 200. Furthermore, FIG. 4 illustrates an example connector for connecting the combination of multiple sensing members in forming the apparatus 100. FIG. 5 illustrates a system comprising the apparatus 100. In as much as the construction and arrangement of the apparatus 100 various associated elements may be well-known to those skilled in the art, it is not deemed necessary for purposes of acquiring an understanding of the present disclosure that there be recited herein all of the constructional details and explanation thereof. Rather, it is deemed sufficient to simply note that as shown in FIGS. 1 to 5, in the apparatus 100 and its arrangement with the duct 200 or with any other system, only those components are shown that are relevant for the description of various embodiments of the present disclosure.

As shown in FIGS. 1 to 4, the apparatus 100 includes a mounting attachment 110 and at least one combination of multiple sensing members 130 configured to the mounting attachment 110. The mounting attachment 110 includes a conduit member 120, which defines through hollow and elongated configuration, and has first and second end portions 112, 114 opposite to each other, seen in FIGS. 3A and 3B. Each of the first and second end portions 112, 114 of the conduit member 120 has an opening 116. In one embodiment, the conduit member 120 may be a through hollow pipe made of suitable material, such as metal or ceramic etc., that has capability to withstand high temperature up to the level of the temperature of flowable medium flowing through the duct 200. The apparatus 100 is mountable to the duct 200 for analysis for flowable medium flowing through the duct 200, in a direction as shown by arrow 'A,' in FIG. 3A, using the mounting attachment 110.

To mount the apparatus 100 with the duct 200, the mounting attachment 110 comprises a fixture arrangement 140, seen in FIGS. 3A and 3B. The fixture arrangement 140 may releasably and movably mount the mounting attachment 110 to the duct 200. In one embodiment, the fixture arrangement 140 may include a bolt-flange assembly 142 and a slip-fit assembly 144. The bolt-flange assembly 142 may releasably attach the first end portion 112 of the conduit member 120 to the duct 200. Further, the slip-fit assembly 144 may releasably and movably attach the second end portion 114 of the conduit member 120 to the duct 200. The slip-fit assembly 144 may enable movement of the second end portion 114 to adjust differential length of the conduit member 120 versus the duct 200 which arises due to heating effect of the flowable medium flowing through the duct 200.

The apparatus 100 includes at least one combination of multiple sensing members 130 that may be disposed on the conduit member 120. In one embodiment, one combination of multiple sensing members 130 may be disposed on the conduit member 120 at any desired location as per the requirement, however, in another embodiment, a plurality of combination of multiple sensing members 130 may be disposed spaced apartly across the conduit members 120. As shown in example FIGS. 1 and 3A, three (3) and two (2), respectively, such combination of multiple sensing members 130 are disposed spaced apartly across the conduit members 120, however, without departing from the scope of the present disclosure any required number of such combination of multiple sensing members 130 across the conduit members 120. The combination of multiple sensing members 130 is capable of determining various parameters related to the flowable medium flowing through the duct 200.

An example FIG. 2 illustrates the combination of multiple sensing members 130 as per one embodiment of the present disclosure. The combination of multiple sensing members 130 may include at least one oxygen sensing element 132 and at least one temperature sensing element 134 to respectively determine a level of oxygen in the flowable medium and the temperature of the flowable medium flowing through the duct 200.

In one embodiment of the present disclosure, the combination of multiple sensing members 130 may include two oxygen sensing element 132 and one temperature sensing element 134 disposed between the two oxygen sensing element 132. In such embodiment, the oxygen sensing element 132 may be an automotive heated Zirconium oxide sensor, and the temperature sensing element 134 may be a thermocouple. However, without departing from the scope of the present disclosure, any other oxygen sensing element or temperature sensing element, other than the disclosed ones may be utilized as per the requirement.

The combination of multiple sensing members 130 may be disposed on the conduit member 120. The combination of multiple sensing members 130 may directly be coupled to the conduit member 120 or may be coupled through suitable connectors as per the requirement.

In an example embodiment, as shown in FIG. 4, the combination of multiple sensing members 130 may be coupled to the conduit member 120 by utilizing suitable connector, such as a connector 136. The connector 136 couples the combination of multiple sensing members 130 with the conduit member 120 in such a manner that the through hollow configuration of the conduit member 120 remains. For example, the connector 136 may be a T-shaped hollow threaded connector that includes two opposite threaded lateral openings 136a, 136b and a threaded transversal opening 136c. The lateral openings 136a, 136b couple the conduit member 120, and the transversal opening 136c incorporates the combination of multiple sensing members 130. To couple the connector 136 with the conduit member 120 from across the lateral openings 136a, 136b, the conduit member 120 may need to be bifurcated into two parts and threaded to be incorporated across the threaded lateral openings 136a, 136b.

In FIGS. 3A and 3B, an arrangement 300 between the apparatus 100 and the duct 200 having a cross-section 202 for determining parameters of the flowable medium flowing through the duct 200 is depicted. As shown, a plurality of apparatuses, such as the apparatuses 100 are adapted to be arranged across the cross-section 202 of the duct 200 in a spaced relation. Such arrangement of the various apparatuses 100 defines a grid 310 across the cross-section 202 of the duct 200. Each apparatus 100 are arranged to the duct 200, and releasably and movably mounted to the duct 200 through the fixture arrangement 140. Specifically, firstly, the conduit member 120 in each apparatus 100 is inserted entirely into the duct 200 via aligned opposite holes 204 configured on the duct 200, such that the openings 116 at of the first and second end portions 112, 114 match with the respective aligned opposite holes 204.

Secondly, each end portions 112 and 114 of the respective conduit member 120 in the respective apparatus 100 are coupled utilizing respectively the bolt-flange assembly 142 and the slip-fit assembly 144 of the fixture arrangement 140. Specifically, the bolt-flange assembly 142 is adapted to releasably attach the first end portion 112 of the conduit member 120 to the duct 200 across one of the hole 204, and the slip-fit assembly 144 is adapted to releasably and movably attach the second end portion 114 of the conduit member 120 to the duct 200 across the other hole 204, wherein the slip-fit assembly 144 enables movement of the second end portion 114 to adjust differential length of the conduit member 120 arises due to heating effect of the flowable medium flowing through the duct 200. Coupling of the opened first and second end portions 112, 114 of the conduit member 120 to the duct 200 across the opposite holes 204 defines a passageway 122 of the conduit member 120.

In one embodiment of the present disclosure, the passageway 122 is capable of enabling a fluid to flow in a direction as shown by arrow 'B,' in FIG. 3A, to cool the apparatus 100 and its components, which may be heated by the heated flowable medium flowing through the duct 200. In one embodiment of the present disclosure, each of the bolt-flange assembly 142 may include a fan 146 configured at the first end portion 112 along the opening 116 for regulating the desired fluid flow through the passageway 122.

Coupling of the various conduit members 120 with the duct 200 forms two dimensional grid 310 across the entire cross-section 202 of the duct 200. The combination of multiple sensing members 130 on each conduit members 120, forming such grid 310, is located within the duct 200 to directly be in contact with the flowable medium flowing though the duct 200. The grid 310 enables determination of a plurality of data with respect to the level of oxygen and the temperature of the flowable medium from side-to-side or top-to-bottom across the entire cross-section 202 of the duct 200. As mentioned above, at each location of the combination of multiple sensing members 130 on the conduit member 120, two oxygen sensing element 132, such as automotive heated zirconium oxide sensor, and one temperature sensing element 134, such thermocouple is provided.

In another embodiment of the present disclosure, the fluid flowing through the passageway 122, apart from cooling the apparatus 100 and its components as described above, is capable of serving as a reference for the oxygen via the sensing members 132, particularly, the automotive zirconium oxide sensors. zirconium oxide sensors work by comparing the percentage or oxygen on two sides of the sensors, i.e. percentage of oxygen in the flowable medium flowing through the duct 200 verses fluid flowing through the passageway 122. The reference fluid is drawn by the fan 146 into the passageway 122 at the sensing members 132 area. The reference fluid is also used when verifying whether or not the sensing members 132 are working, and to periodically calibrate thereto online. In one embodiment, an air nozzle member 150 (as shown in FIG. 4) may be utilized for injecting calibration reference fluids for sensor calibration and verifying sensor working condition.

The same air nozzle member 150, in another embodiment, may also be utilized to control dust deposition on the combination of multiple sensing members 130 in order to minimize fouling and plugging thereof. The air nozzle member 150 may be configured to the mounting attachment 110 to periodically clean the combination of multiple sensing members 130 to control dust deposition and also be utilized for injecting calibration reference fluid for calibration and verifying sensor working condition. In further embodiment, for preventing dust deposition on the combination of multiple sensing members 130, a protective filter member 160 may also be configured to be installed over the combination of multiple sensing members 130 to control dust deposition. The protective filter member 160 may be a porous mesh finer than the particles flowing with the flowable medium.

Several such oxygen sensing element 132 and thermocouple 134 across the grid 310 allow several forms of on-line checking. The oxygen concentration at each location within the duct 200 is expected to vary over time, sometimes rapidly as combustion condition changes. The two oxygen sensing elements 132 at a particular location in the duct 200 may give almost identical average readings over a period of several seconds. Comparing instantaneous readings of the two oxygen sensing elements 132 at each location can detect if one oxygen sensing elements 132 out of the two have failed or become plugged due to ash or other contaminants present in the flowable medium. Such plugged sensing elements will change value more slowly than a clean sensing element. Failed sensing elements 132 may provide a steady or off-scale value.

Similar comparison, with a wider tolerance, may be made across the oxygen sensing elements 132 at different locations in the duct 200. For example, if large quantities of ash are carried in the flowable medium at a bottom of the duct 200, the lower elevation oxygen sensing elements 132 across the grid 310 may plug up while the upper elevation oxygen sensing elements 132 in the duct 200 are clean.

Thermocouples 134 are less likely to have failures due to fouling and may or may not be duplicated at each measurement location.

Referring now to FIG. 5, which illustrates a block diagram depicting a system 400 for determining parameter of the flowable medium flowing through the duct 200. The system 400 will be described in conjunction to FIGS. 1 to 4, and reference of various elements is taken therefrom while describing FIG. 5. The system 400 incorporates the arrangement 300 between the apparatus 100 and the duct 200, as described above, to electrically couple thereto with an electronic module 410. Specifically, the combination of multiple sensing members 130 in the apparatus 100 is electrically coupled to the electronic module 410.

The electronic module 410 is adapted to analyze a pattern of the at least one of the level of oxygen and the temperature of the flowable medium across the cross-section 202 of the duct 200 based on the plurality of data in relation to the at least one parameter, such as the level of oxygen in the flowable medium and the temperature of the flowable medium. Such an electrical coupling between the electronic module 410 and the combination of multiple sensing members 130 is enabled by wirings, which passes through the passageway 122 of the conduit member 120 and may be cooled by the fluid flow upon being heated by the heated flowable medium flowing through the duct 200.

Throughout the disclosure, it is described that the parameter of a flowable medium that may be determined are oxygen level and temperature of the flowable medium using said suitable sensing members. However, the disclosure is not intended to limit its scope for only measuring oxygen level and temperature of the flowable medium, but it extends to include, with departing from the scope of the present disclosure, any or other additional parameters, such as level of carbon monoxide in flowable medium or flow velocity of the flowable medium or other related parameter that may also be determined by the system upon arrangement of suitable sensing member. In such embodiment, the at least one combination of multiple sensing members 130 may include at least one auxiliary sensing element (not shown) to determine additional parameters, such as level of carbon monoxide in the flowable medium or flow velocity of the flowable medium or other related parameter. The auxiliary sensing element may be similarly configured as other sensing member with the apparatus 100.

The apparatus, arrangement and the system for determining at least one parameter of a flowable medium flowing through a duct of the present disclosure are advantageous in various scopes. The apparatus has accuracy of temperature determination of flowable medium and capable of having freedom of choice of selection to determine variable parameters of the flowable medium. Further, the apparatus is capable of being placed or arranged with a duct in economical and convenient to use to form a grid for accurately determining the various data related to the flowable medium. Such grid of measurement points gives more accurate average values than one or two sensors as used in conventional ducts, and allows the detection of side-to-side or top-to-bottom flow imbalances, and provides enough redundancy that reasonable measurements may still be provided after a few sensing members in the grid are failed.

Further, combining various sensing members, such as oxygen sensing members and temperature sensing members provide several benefit over separate sensors as used conventionally. For example, a minimum number of new mounting assemblies and penetration into the duct are required. Such mounting arrangement permits additional measurement points to be added to the grid at relatively low cost by increasing the number of sensing members in each conduit member. Further, single electronic module and common power supply with control electronics supports multiple sensing members with a single connection. Furthermore, the smaller number of mounting assemblies and external wiring reduce installation time and cost as compared to the conventional sensor fittings. The apparatus may also be easily disassembled and transported to the site of installation. The apparatus and method are convenient to use and economical. Various other advantages and features of the present disclosure are apparent from the above detailed description and appendage claims.

The foregoing descriptions of specific embodiments of the present disclosure have been presented for purposes of illustration and description. They are not intended to be exhaustive or to limit the present disclosure to the precise forms disclosed, and obviously many modifications and variations are possible in light of the above teaching. The embodiments were chosen and described in order to best explain the principles of the present disclosure and its practical application, to thereby enable others skilled in the art to best utilize the present disclosure and various embodiments with various modifications as are suited to the particular use contemplated. It is understood that various omission and substitutions of equivalents are contemplated as circumstance may suggest or render expedient, but such are intended to cover the application or implementation without departing from the spirit or scope of the claims of the present disclosure.

What is claimed is:

1. An apparatus mountable to a duct having a cross-section, for determining at least one parameter of a flowable medium flowing through the duct, the apparatus, comprising:
   a conduit member, defining first and second end portions opposite to each other, each of the first and second end portions having an opening, wherein the conduit member comprises a through hollow and elongated configuration configured to transversely extend entirely into the duct via aligned opposite holes such that each of the holes matches the respective openings to thereby define a passageway to enable a fluid flow therethrough apart from the flowable medium flowing through the duct; and
   at least one combination of multiple sensing members adapted to be disposed on the conduit member within the duct, and to be in contact with the flowable medium flowing though the duct, wherein the at least one combination of multiple sensing members comprises,
      at least one oxygen sensing element to determine a level of oxygen in the flowable medium flowing through the duct, and
      at least one temperature sensing element to determine the temperature of the flowable medium flowing through the duct.

2. The apparatus as claimed in claim 1, wherein the at least one combination of multiple sensing members comprises a plurality of combination of multiple sensing members disposed spaced apart across the conduit member located within the duct to determine respective parameters across the entire diameter of the duct.

3. The apparatus as claimed in claim 1, further comprising a connector to couple the at least one combination of multiple sensing members with the conduit member such that the through hollow configuration of the conduit member remains.

4. The apparatus as claimed in claim 3, wherein the conduit member is bifurcated; and wherein the connector is a T-shaped hollow threaded connector that comprises two opposite lateral openings and a transversal opening, wherein the lateral openings couple to the conduit member, and the transversal opening incorporates the least one combination of multiple sensing members, and wherein the T-shaped hollow threaded connector is coupled to the bifurcated conduit member.

5. The apparatus as claimed in claim 1, wherein the at least one combination of multiple sensing members comprises two oxygen sensing elements and one temperature sensing element disposed therebetween.

6. The apparatus as claimed in claim 1, wherein the at least one oxygen sensing element is an automotive heated zirconium oxide sensor.

7. The apparatus as claimed in claim 1, wherein the fluid flowing through the passageway apart from the flowable medium flowing through the duct, is a reference fluid.

8. The apparatus as claimed in claim 1, wherein the mounting attachment comprises a fixture arrangement to releasably and movably mount the mounting attachment to the duct across each of the holes, the fixture arrangement comprising:
   a bolt-flange assembly adapted to releasably attach the first end portion of the conduit member to the duct across one of the hole; and
   a slip-fit assembly adapted to releasably and movably attach the second end portion of the conduit member to the duct across the other hole, wherein the slip-fit assembly enables movement of the second end portion to adjust differential length of the conduit member versus the duct.

9. The apparatus as claimed in claim 8, wherein the bolt-flange assembly comprises a fan configured at the first end portion along the opening for regulating a desired fluid flow through the passageway apart from the flowable medium flowing through the duct.

10. The apparatus as claimed in claim 9, wherein the passageway is capable of enabling the fluid from the fan to flow therethrough apart from the flowable medium flowing through the duct to cool the apparatus, when heated due to a heating effect of the flowable medium flowing through the duct.

11. The apparatus as claimed in claim 9, wherein the passageway is capable of enabling the fluid from the fan to flow therethrough apart from the flowable medium flowing through the duct to serve as the reference fluid for the parameter determination by the sensing members.

12. The apparatus as claimed in claim 11, wherein the sensing member, based on the fluid flow from the fan flowing through the passageway is configured and adapted to compare a percentage of parameter determined by the sensing member in the flowable medium flowing through the duct verses a percentage of parameter of the fluid flowing through the passageway.

13. The apparatus as claimed in claim 1 further comprising an air nozzle member disposed on the conduit to periodically clean the at least one combination of multiple sensing members.

14. The apparatus as claimed in claim 1 further comprising a protective filter member configured to be installed over the at least one combination of multiple sensing members.

15. The apparatus as claimed in claim 1 wherein the at least one combination of multiple sensing members comprises at least one auxiliary sensing element to determine the at least one parameter of flowable medium flowing through the duct.

16. An arrangement for determining at least one parameter of a flowable medium flowing through a duct having a cross-section, the arrangement comprising:
a plurality of apparatuses adapted to be arranged across the cross-section of the duct in a spaced relation to define a grid across the cross-section, wherein each of the plurality of apparatus comprises,
a conduit member defining first and second end portions opposite to each other, each of the first and second end portions has an opening, wherein the conduit member comprises a through hollow and elongated configuration configured to transversely extend entirely into the duct via aligned opposite holes such that each of the holes matches the respective openings to define a passageway to enable a fluid flow therethrough apart from the flowable medium flowing through the duct; and
at least one combination of multiple sensing members adapted to be disposed on the conduit member, the at least one combination of multiple sensing members being in contact with the flowable medium flowing though the duct to determine respective parameters of the flowable medium, wherein the at least one combination of multiple sensing members comprises,
at least one oxygen sensing element to determine a level of oxygen in the flowable medium flowing through the duct, and
at least one temperature sensing element to determine the temperature of the flowable medium flowing through the duct.

17. The arrangement as claimed in claim 16, wherein the grid formed by the plurality of apparatuses within the duct detects a level of oxygen and temperature of the flowable medium across the entire cross-section of the duct through the at least one combination of multiple sensing members.

18. The arrangement as claimed in claim 16, wherein the grid defines a plurality of locations across the length of the duct and detects a level of oxygen and temperature of the flowable medium across the entire cross-section of the duct.

19. A system for determining at least one parameter of a flowable medium flowing through a duct having a cross-section, the system, comprising:
an arrangement between the duct and a plurality of apparatuses, wherein the plurality of apparatuses is arranged across the cross-section of the duct in a spaced relation defining a grid across the cross-section, wherein each of the plurality of apparatuses, comprises,
a conduit member defining first and second end portions opposite to each other, each of the first and second end portions has an opening, wherein the conduit member comprises a through hollow and elongated configuration configured to transversely extend entirely into the duct via aligned opposite holes such that each of the holes matches the respective openings to thereby define a passageway to enable a fluid flow therethrough apart from the flowable medium flowing through the duct; and
at least one combination of multiple sensing members adapted to be disposed on the conduit member, the at least one combination of multiple sensing members is located within the duct to directly being in contact with the flowable medium flowing though the duct to determine the respective parameters of the flowable medium, the at least one combination of multiple sensing members having,
at least one oxygen sensing element to determine a level of oxygen in the flowable medium flowing through the duct, and
at least one temperature sensing element to determine the temperature of the flowable medium flowing through the duct;
and
an electronic module electrically coupled to each of the at least one combination of multiple sensing members.

20. The system as claimed in claim 19, wherein the electronic module is coupled to the sensing members via conductive wires, disposed through the passageway of the conduit member and is cooled by the fluid flow in the passageway upon being heated by the heated flowable medium flowing through the duct.

* * * * *